(12) United States Patent
Simons et al.

(10) Patent No.: US 12,171,997 B2
(45) Date of Patent: Dec. 24, 2024

(54) SYSTEM AND METHOD OF SLEEP INDUCTION

(71) Applicant: Teledyne Scientific & Imaging, LLC, Thousand Oaks, CA (US)

(72) Inventors: Stephen B. Simons, Raleigh, NC (US); Patrick M. Connolly, Cary, NC (US); Renee Shimizu, Raleigh, NC (US); Alexandra Yanoschak, Morrisville, NC (US); Calvin Schmidt, Durham, NC (US); Michael Weisend, Efland, NC (US)

(73) Assignee: TELEDYNE SCIENTIFIC & IMAGING, LLC, Thousand Oaks, CA (US)

( * ) Notice: Subject to any disclaimer, the term of this patent is extended or adjusted under 35 U.S.C. 154(b) by 1003 days.

(21) Appl. No.: 17/160,442

(22) Filed: Jan. 28, 2021

(65) Prior Publication Data

US 2021/0236806 A1     Aug. 5, 2021

Related U.S. Application Data

(60) Provisional application No. 62/969,835, filed on Feb. 4, 2020.

(51) Int. Cl.
*A61N 1/04* (2006.01)
*A61B 5/00* (2006.01)
(Continued)

(52) U.S. Cl.
CPC ........... *A61N 1/0456* (2013.01); *A61M 21/02* (2013.01); *A61N 1/0484* (2013.01); *A61N 1/08* (2013.01);
(Continued)

(58) Field of Classification Search
CPC ...... A61N 1/0456; A61N 1/0484; A61N 1/08; A61N 1/36031; A61N 1/36034;
(Continued)

(56) References Cited

U.S. PATENT DOCUMENTS

2015/0374971 A1   12/2015   Dar et al.
2016/0074657 A1   3/2016   Kwan et al.
(Continued)

FOREIGN PATENT DOCUMENTS

WO   WO-2018051354 A1 *  3/2018   ........... A61B 5/0205

OTHER PUBLICATIONS

Extended European Search Report for European Application No. 21153958.0 completed Jun. 21, 2021.
(Continued)

*Primary Examiner* — Thaddeus B Cox
*Assistant Examiner* — Joshua D Lannu
(74) *Attorney, Agent, or Firm* — K&L Gates LLP

(57) ABSTRACT

A sleep induction device includes a headband, multiple transcranial stimulation electrodes, and control electronics to drive the electrodes. The sleep induction device may be worn by an awake user prior to attempting sleep. The control electronics are configured to cause the stimulation electrodes to emit a sequence of stimulation waveforms separated by interstimulus periods. The stimulation waveforms may have the characteristics of low-delta waveforms that may characterize non-REM stage 3 sleep. The stimulation period may last from about 4-8 seconds and the interstimulus period may last from about 10 to 30 seconds. A sleep induction session may include multiple alternating stimulation and non-stimulation periods. The sleep induction session may last for about 5 minutes to about 30 minutes.

15 Claims, 10 Drawing Sheets

(51) Int. Cl.
  *A61B 5/374* (2021.01)
  *A61M 21/00* (2006.01)
  *A61M 21/02* (2006.01)
  *A61N 1/08* (2006.01)
  *A61N 1/36* (2006.01)

(52) U.S. Cl.
  CPC . *A61N 1/36031* (2017.08); *A61M 2021/0027* (2013.01); *A61M 2021/0044* (2013.01); *A61M 2021/0072* (2013.01); *A61M 2021/0083* (2013.01)

(58) Field of Classification Search
  CPC .............. A61N 1/36025; A61M 21/02; A61M 2021/0027; A61M 2021/0044; A61M 2021/0072; A61M 2021/0083; A61M 2205/0216; A61M 2205/3375; A61M 2205/3569; A61M 2205/3592; A61M 2205/505; A61M 2205/52; A61M 2205/581; A61M 2205/583; A61M 2205/587; A61M 2205/80; A61M 2209/088; A61M 2210/06; A61M 2230/10; A61B 5/374; A61B 5/4812; A61B 5/4836; A61B 5/6803
  See application file for complete search history.

(56) References Cited

U.S. PATENT DOCUMENTS

| | | | |
|---|---|---|---|
| 2016/0136424 A1* | 5/2016 | Watt | A61N 1/36025 607/45 |
| 2019/0282812 A1* | 9/2019 | Simons | A61N 1/20 |

OTHER PUBLICATIONS

Cellini et al., Short Duration Repetitive Transcranial Electrical Stimulation During Sleep Enhances Declarative Memory of Facts, Front. Hum. Neurosci., Apr. 12, 2019, 13 pages.

Marshall et al., Boosting slow oscillations during sleep potentiates memory, Nature, vol. 444, Nov. 30, 2006, 4 pages.

Shimizu et al., Closed-Loop Targeted Memory Reactivation during Sleep Improves Spatial Navigation, Frontiers in Human Neuroscience, Feb. 2018, vol. 12, Article 28, 14 pages.

* cited by examiner

SYSTEM AND METHOD OF SLEEP INDUCTION

PRIORITY

The present application claims the benefit of priority under 35 U.S.C. § 119 (e) to U.S. Provisional Application Ser. No. 62/969,835 entitled "SYSTEM AND METHOD OF SLEEP INDUCTION" filed on Feb. 4, 2020, the disclosure of which is herein incorporated by reference in its entirety and for all purposes.

BACKGROUND

Sleep is a necessary activity for humans along with other animals. Sleep may be characterized by a period of inhibited sensory activity, reduced muscle activity especially of the voluntary muscles, and general reduced interactions with the surroundings. Several important physiological functions occur during sleep including, without limitation, restoration processes involved with the metabolism, muscle and bone growth and repair, wound healing, and memory consolidation in the brain. Lack of sleep, or restful sleep, may reduce or interfere with these processes and has also been correlated with cardiovascular disease and diabetes. Conditions that may inhibit sleep or restful sleep may include, without limitation, sleep apnea, bruxism, nocturia, restless-leg syndrome, and insomnia.

Insomnia may relate to either difficulty in falling asleep or waking during normal sleep. Some form of insomnia has been shown in about 10% to about 30% of the general population. However, incidence of insomnia in older adults (age 65 and older) may be much greater and may be in the range of about 50% to 60% of that population. Higher levels of incidence in that age group may be found. According to some investigations, around 60 million people suffer from some form of insomnia in the US alone.

Some methods of addressing insomnia may include the use of medications to help cause or induce sleep. Some examples of such medications may include melatonin, benzodiazepines, sedatives, and sedative/hypnotics such as zolpidem. Melatonin may help a user fall asleep, but sleep onset may occur only about 15 minutes or so faster than without the medication. Users of benzodiazepines and zolpidem may risk psychological or physical dependency among other risks. It is therefore desirable to consider alternatives to medications for inducing sleep which do not have the risks associated with the medications.

SUMMARY

Disclosed are systems and methods for inducing sleep using a time-varying electrical current (transcranial electrical stimulation, or tES) applied to the head of an awake individual. In one aspect, the system and method may include the use of a device worn immediately before going to bed in order to deliver the intervention. The device may require two sets of electrodes wherein the anodes are placed near the top of the forehead bilaterally and approximately over each eye, and the cathodes are placed behind the ear approximately on the mastoid bone ipsilateral to each paired anode. In one example, the electrodes may deliver a slow time-varying current between about 0.5 Hz and about 4 Hz for less than 120 minutes. It is believed that this slow time-varying current may slow down the neural activity and synchronize it to more closely resemble brain states during sleep. In an additional aspect, sensory stimulation may also be applied which may be modulated at the same frequency, or at a harmonic frequency, of the tES. The sensory stimulation signal may be delivered at a consistent time delay with respect to the slow time-varying current of the transcranial stimulation current (that is, the sensory stimulation signal and the transcranial stimulation current may be phase-locked). In some aspects, there may be no time delay between the sensory stimulation signal and the transcranial electrical stimulation signal, and thus the two signals may be delivered in phase. In some other aspects, the time delay between the sensory stimulation signal and the transcranial electrical stimulation signal may result in the two signals being delivered in anti-phase. Sensory stimulation may include any modality of sensory stimulation, which may include a visual or auditory stimulus.

In one aspect, a device for inducing sleep in a waking user, may include a headgear having a headband, a plurality of transcranial stimulation electrodes disposed within the headband, and a control system disposed within the headband and in electrical communication with the plurality of transcranial stimulation electrodes. The control system may further include a processor and a memory device configured to store instructions. The instructions, when executed by the processor, may cause the processor to, in an alternating manner, transmit a transcranial stimulation current to the plurality of transcranial stimulation electrodes for a first period of time and cease transmission of the transcranial stimulation current for a second period of time. The transcranial stimulation current may be characterized by a transcranial stimulation waveform, and the transcranial stimulation waveform may have an amplitude characteristic and a frequency characteristic of a low-delta waveform.

In one aspect, a system for inducing sleep in a waking user may include a mobile communication device and a headgear. The headgear may include a headband, a plurality of transcranial stimulation electrodes, and a control system disposed within the headband and in electrical communication with the plurality of transcranial stimulation electrodes. The control system may further include an antenna configured to receive wireless communications signals from the mobile communication device, a processor in data communication with the antenna, and a memory device. The memory device may be configured to store instructions that, when executed by the processor, cause the processor to receive, via the antenna, one or more signals transmitted by the mobile communication device, transmit a transcranial stimulation current to the plurality of transcranial stimulation electrodes for a first period of time based on the one or more signals received from the mobile communication device, and cease transmission of the transcranial stimulation current for a second period of time based on the one or more signals received from the mobile communication device. The transcranial stimulation current may be characterized by a transcranial stimulation waveform, and the transcranial stimulation waveform may have an amplitude characteristic and a frequency characteristic of a low-delta waveform.

FIGURES

Figure 4:
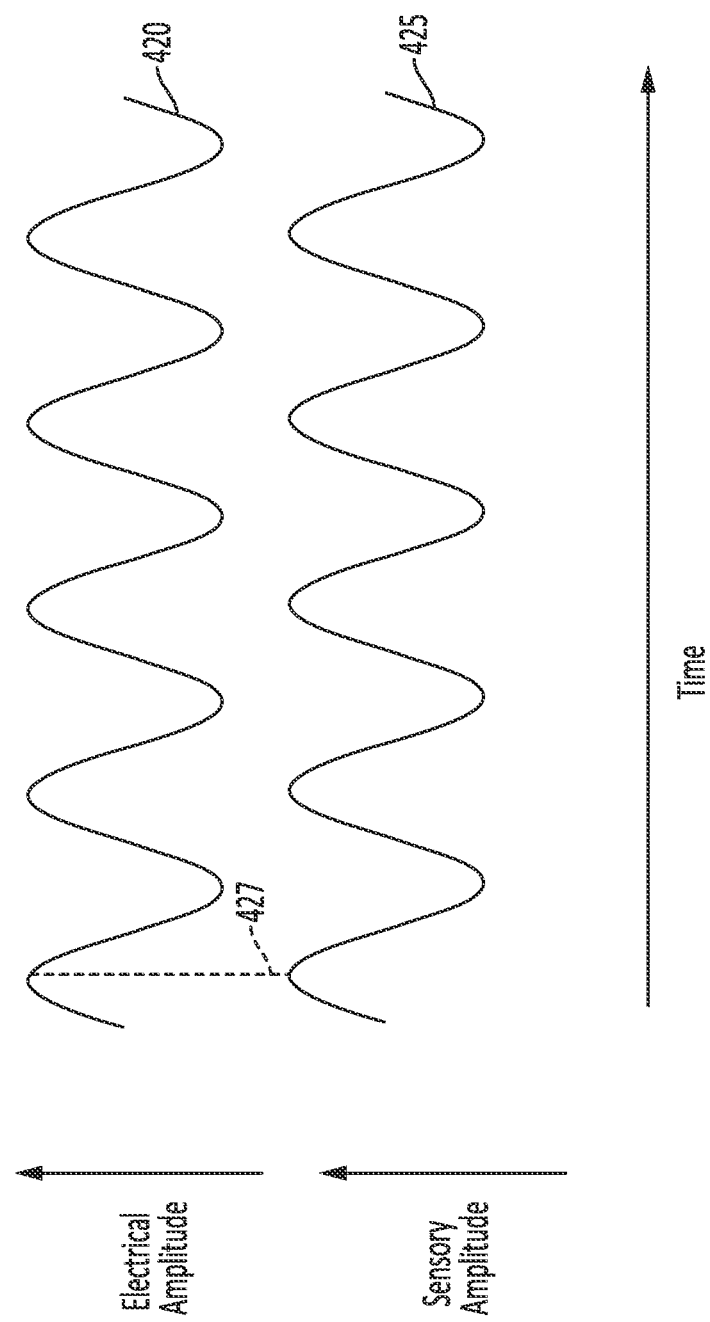

FIG. 4 graphically depicts an application of an electrical stimulus and an application of a sensory stimulus to a user of a sleep induction device according to an aspect of the present disclosure.

Figure 5:
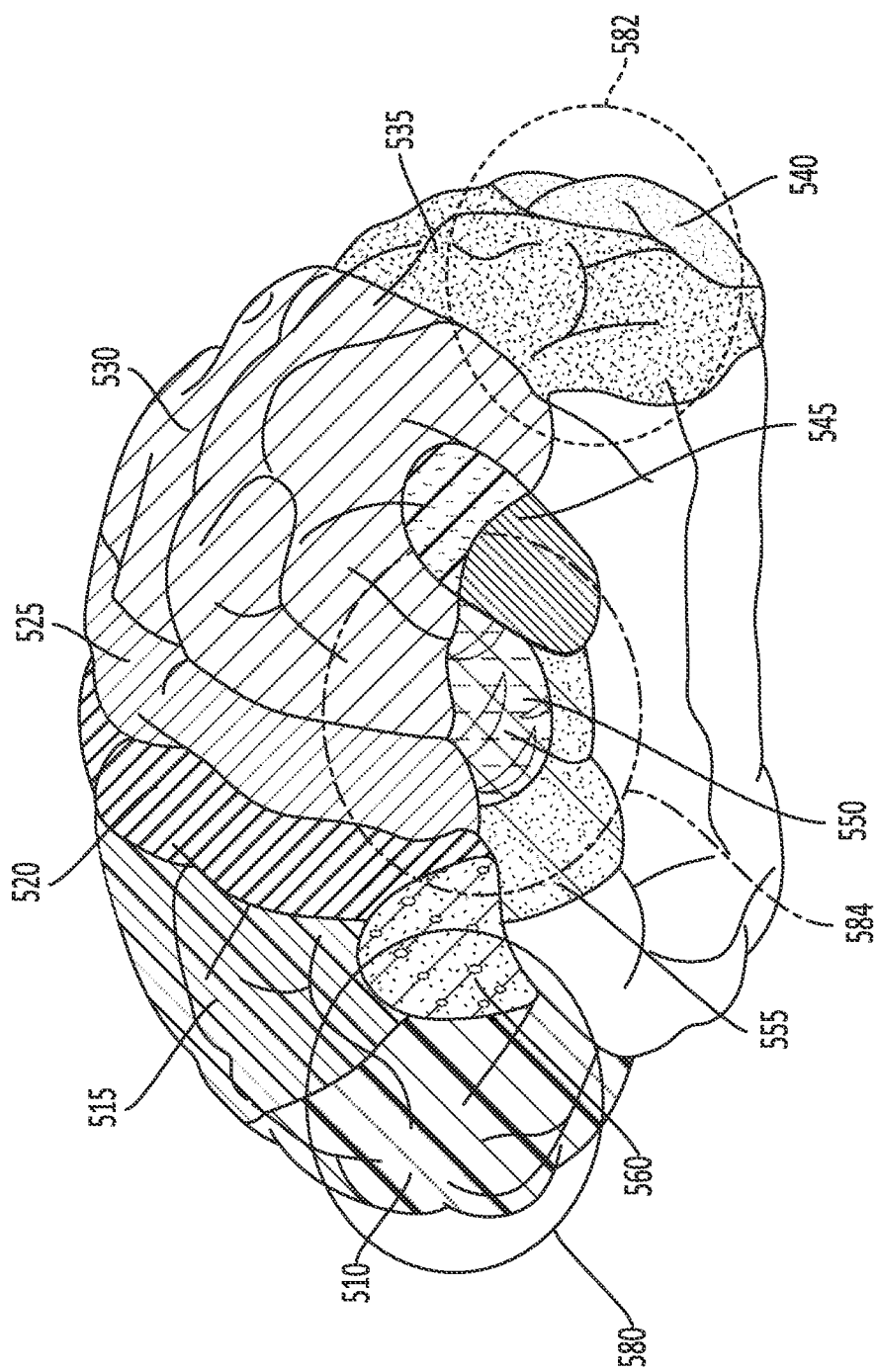

FIG. 5 illustrates a side view of a human brain, depicting various functional regions thereof according to an aspect of the present disclosure.

Figure 6:
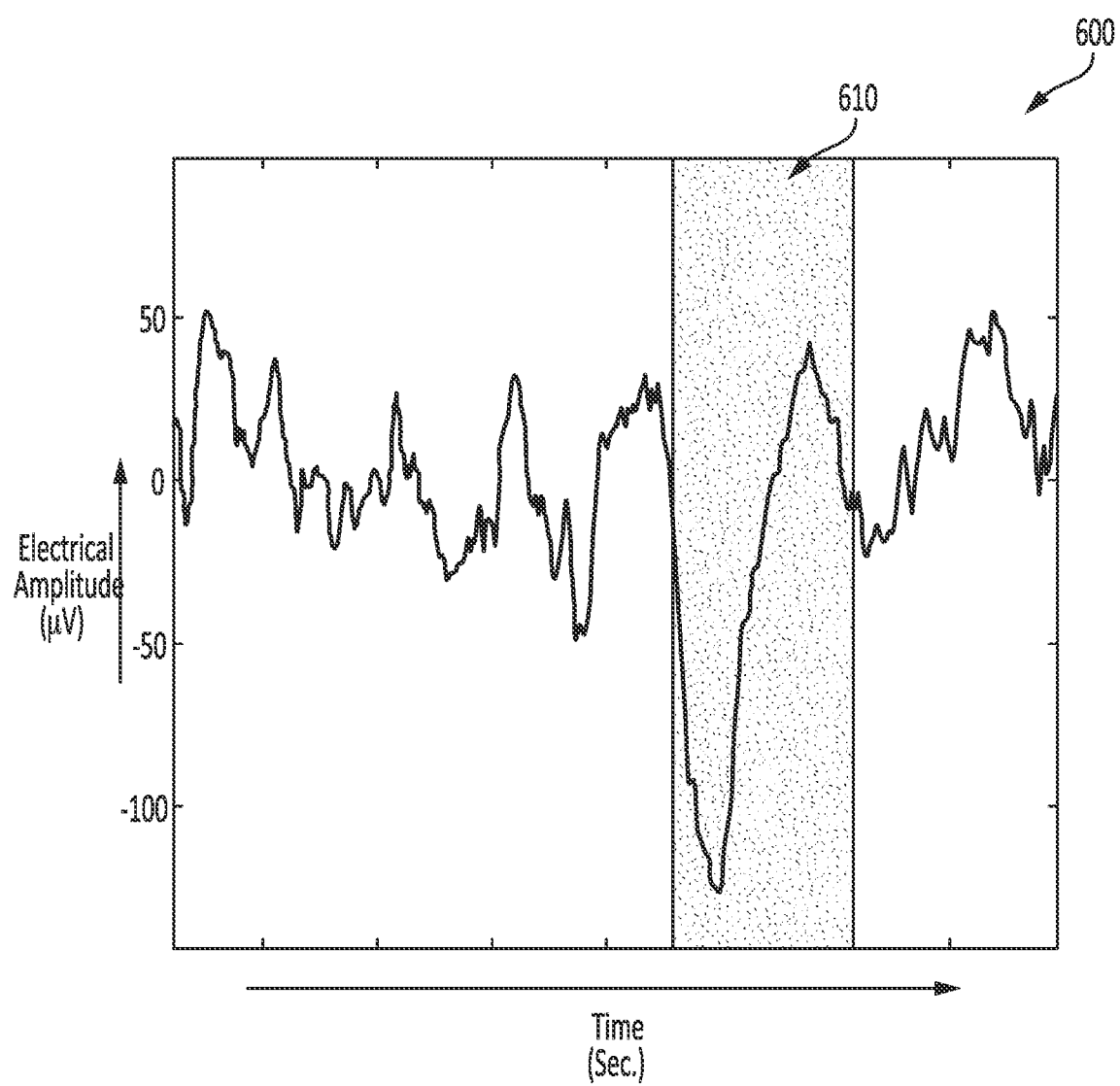

FIG. 6 depicts an example of an EEG recording of a human during non-REM sleep stage 3 according to an aspect of the present disclosure.

Figure 7:
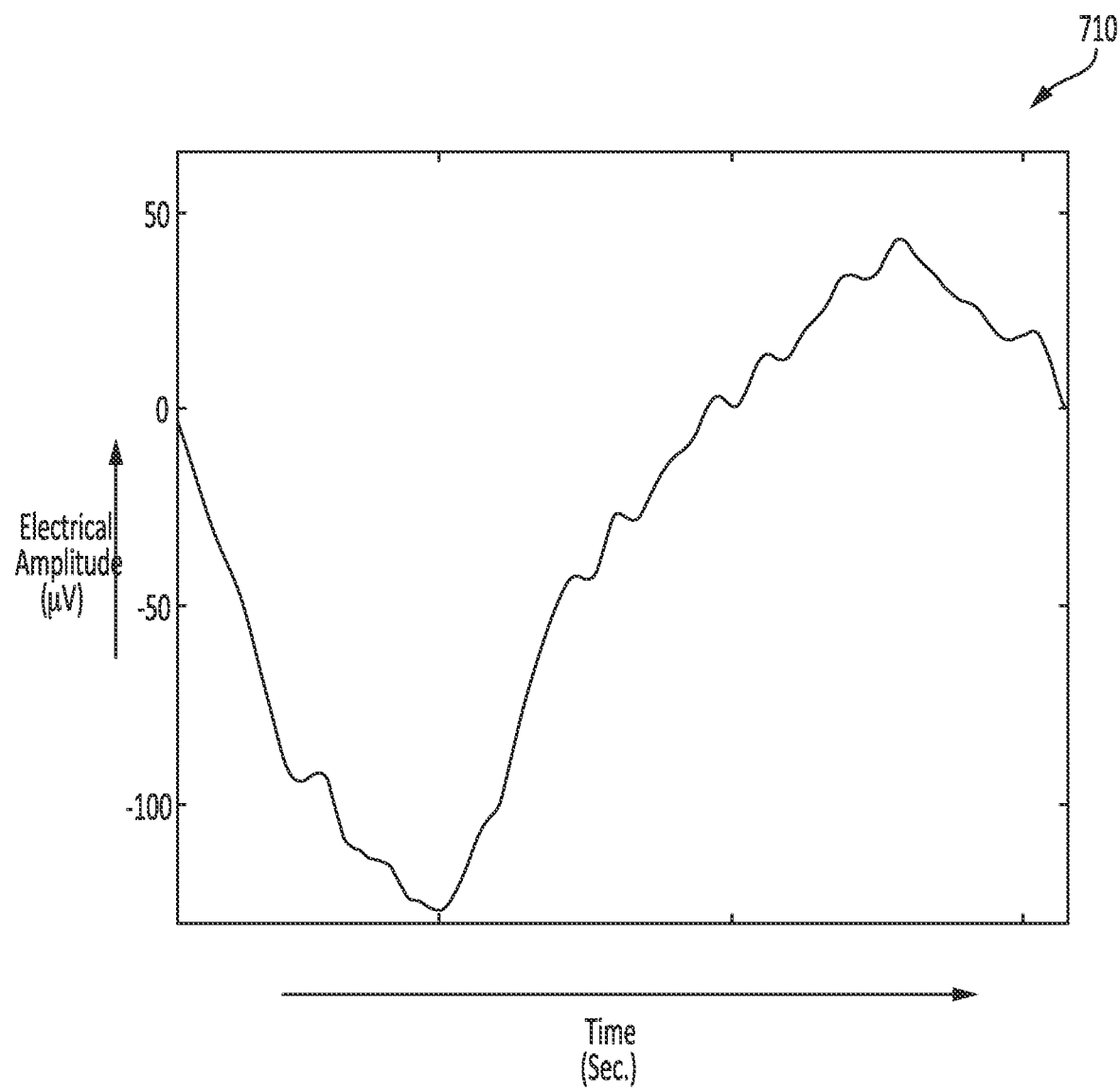

FIG. 7 depicts one aspect of an AC current stimulation waveform according to an aspect of the present disclosure.

Figure 8A:
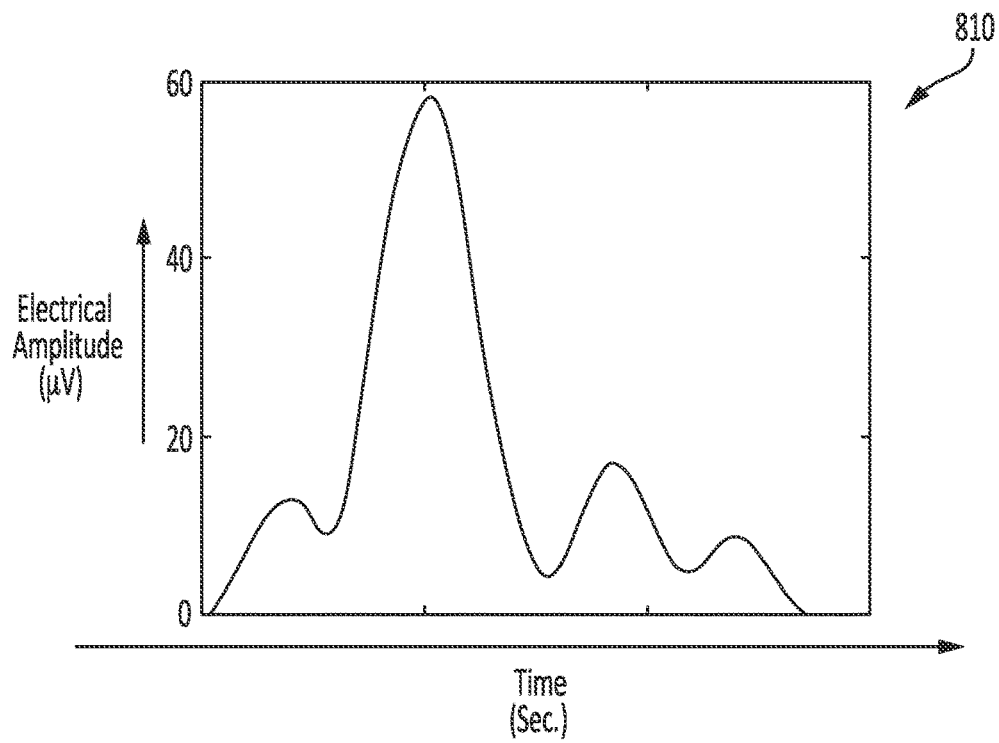
Figure 8B:
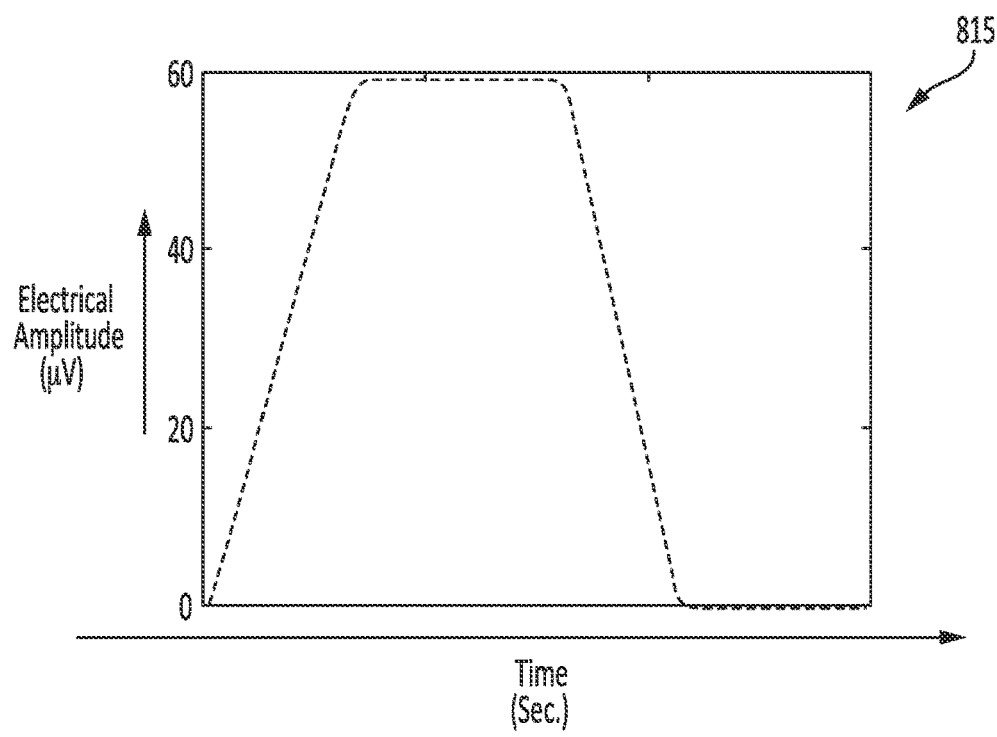

FIGS. 8A and 8B depict aspects of DC current stimulation waveforms according to aspects of the present disclosure.

Figure 9:
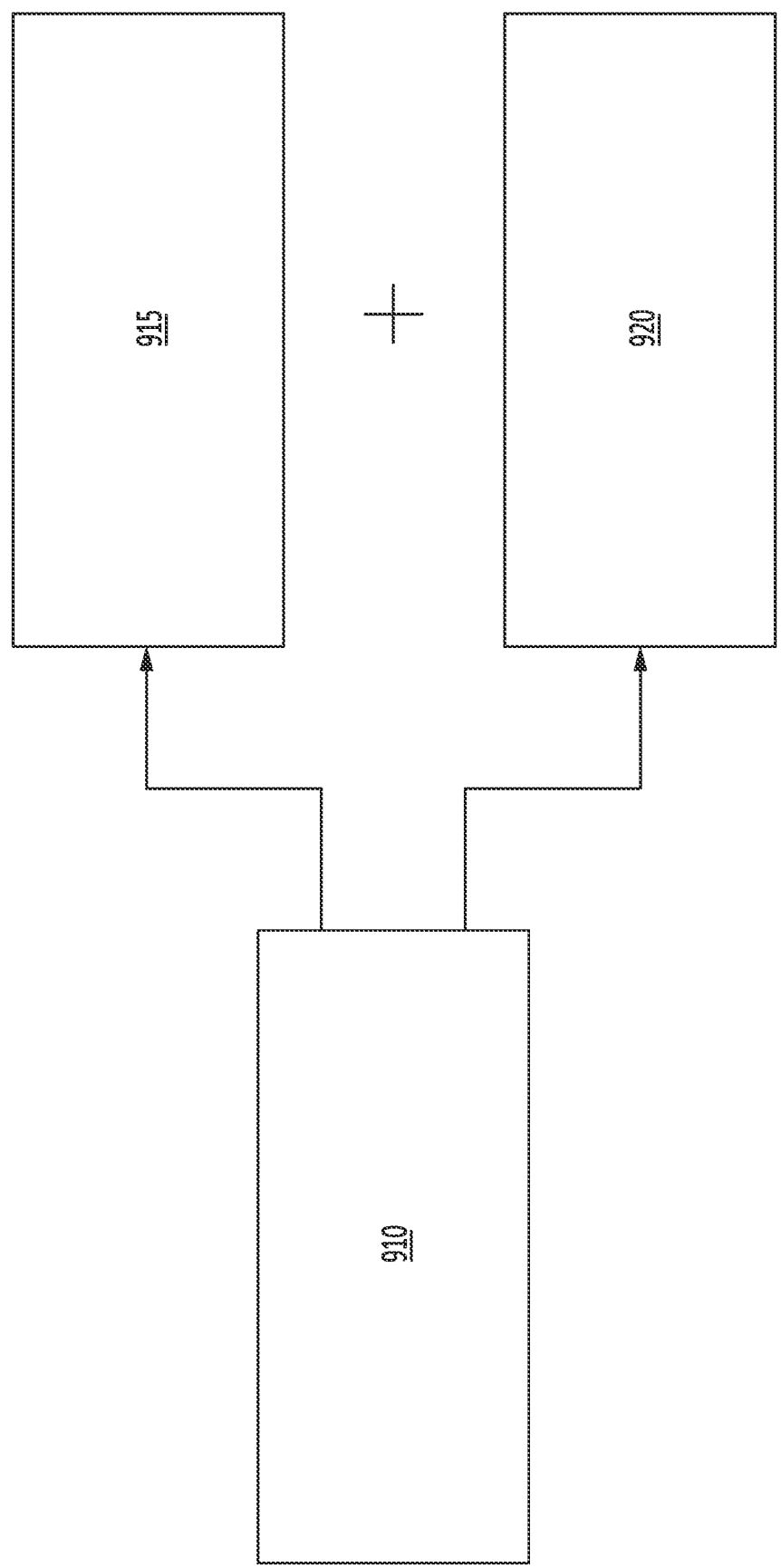

FIG. 9 is a block diagram of a method of use of a sleep induction system that includes the headgear according to an aspect of the present disclosure.

DESCRIPTION

As disclosed above, it is desirable to provide treatments for insomnia that do not rely on medications. Such treatments may not have the same disadvantageous effect of such medications which can include the risk of dependency and untoward interactions with other medications taken by the insomniac. In one potential treatment, the patient may undergo non-invasive transcranial electrical stimulation. Such stimulation may, for example, be composed of electrical waveforms that are similar to those naturally present in the brain while a patient is asleep. It is believed that an external stimulation of an awake brain with waveforms similar to those produced during sleep may make it easier for the brain to produce similar waveforms. In this manner, the brain may be stimulated to initiate the process of entering a sleep state. A system and a method for inducing sleep via non-invasive transcranial electrical stimulation is disclosed herein.

Figure 1:
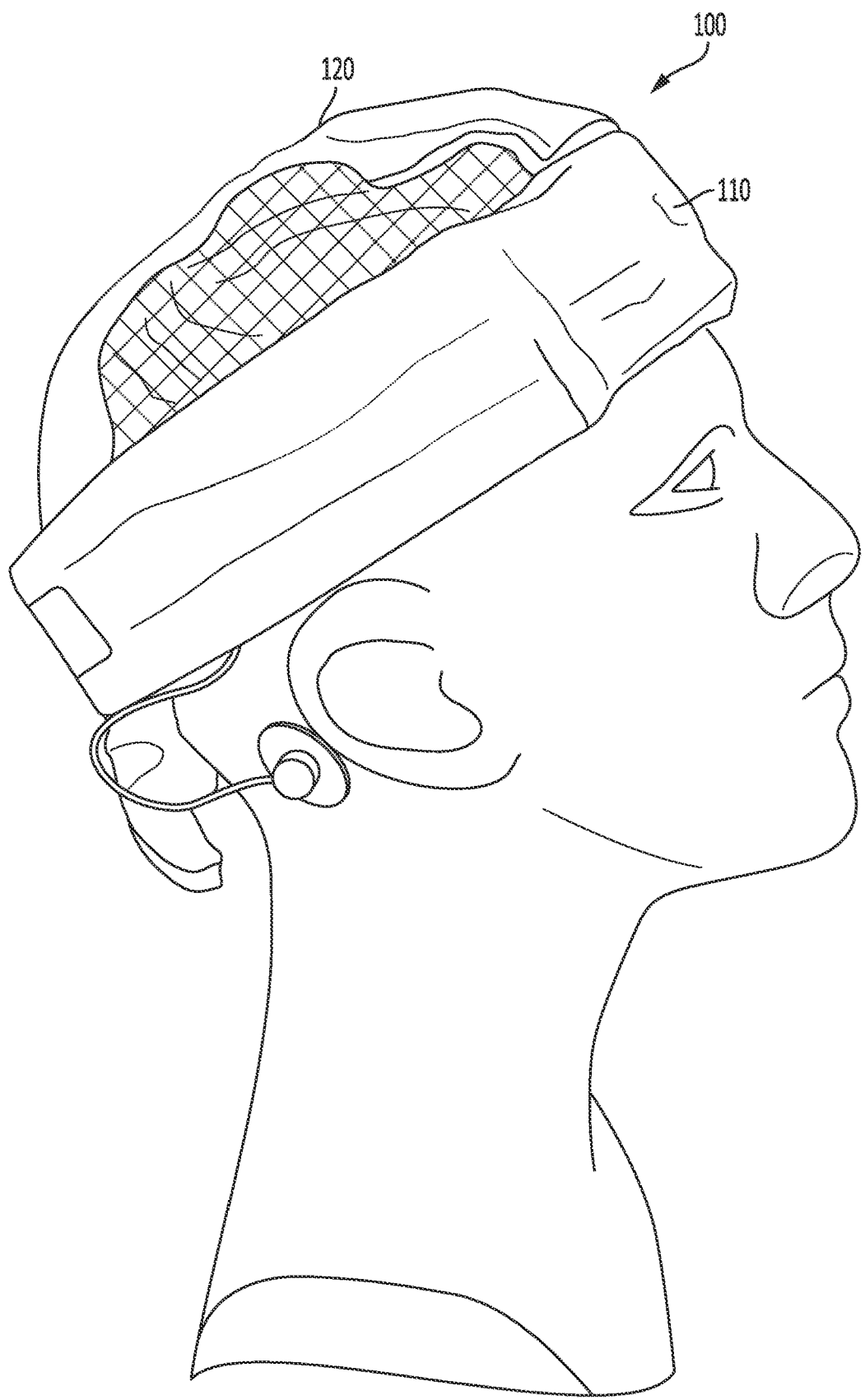
FIG. 1 depicts an example of a user of a sleep induction device with the headgear placed on the head according to an aspect of the present disclosure.

In one aspect, a non-invasive transcranial sleep-inducing system may include headgear configured to be worn by a person while awake and before bedtime. FIG. 1 illustrates an example of such headgear 100 as worn by an awake person before going to bed. The headgear 100 may include a cloth or elastic headband 110, which may be positioned on the forehead and wrap around the circumference of the head. The headband 110 may be made of an elastic material to allow the headband 110 to conform to the shape of the head. The headband 110 may be continuous or may include two end portions (see 240 at FIG. 2), which may be fastened together. The two end portions 240 may be fastened together by one or more means. Such fastenings may include, without limitations, clips, hook-and-loop fasteners, buttons, snaps, or any other type of fastener configured to secure two ends of the cloth or elastic material together. In one aspect, the headband 110 may only include material that wraps around the sides of the head. In another aspect, the headband may also include additional material 120 that crosses over the top of the head and is connected to the portion of the headband 110 in contact with the forehead and a portion of the headband 110 in contact with the back of the head.

Figure 2:
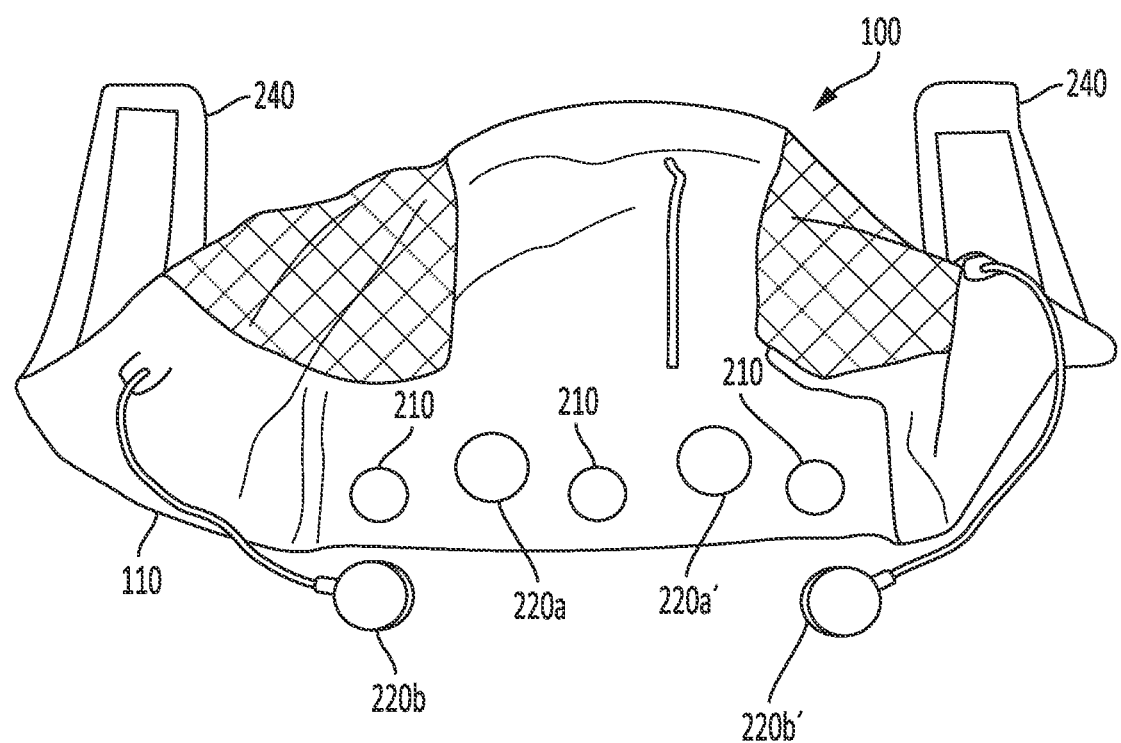
FIG. 2 depicts an example of the headgear of FIG. 1, illustrating several components thereof according to an aspect of the present disclosure.
Figure 2:
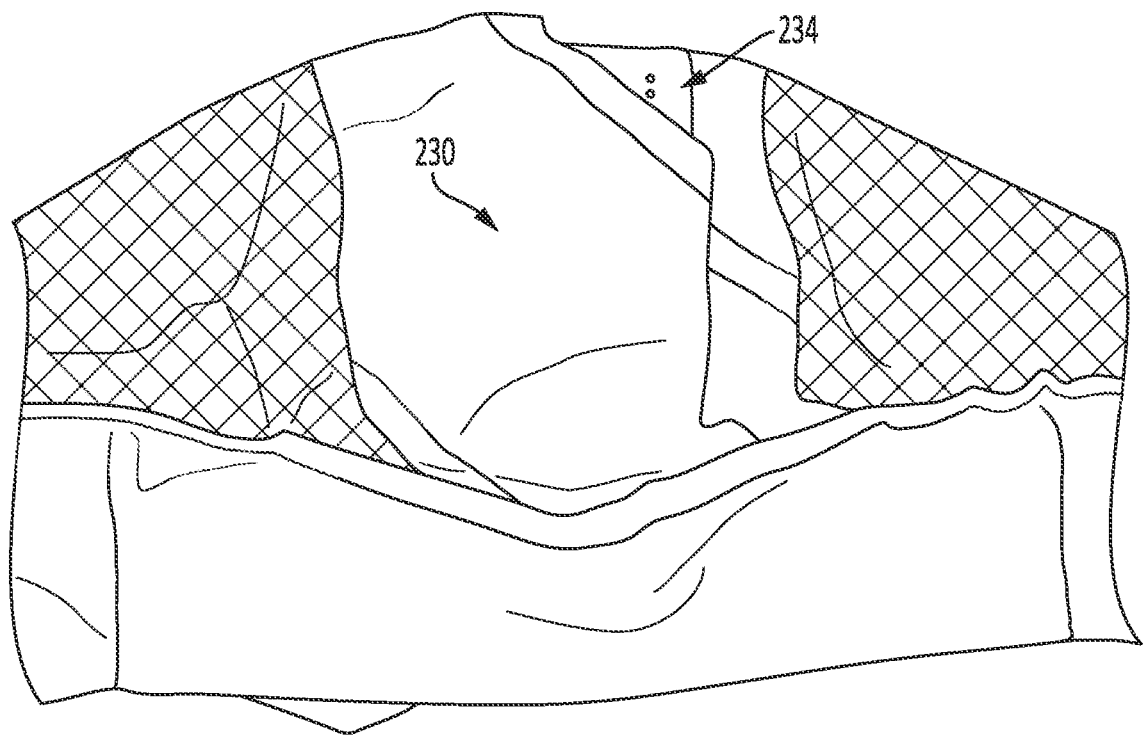

FIG. 2 depicts the headgear 100 of FIG. 1 and illustrates some components thereof. In addition to the headband, the headgear may include one or more EEG electrodes 210 and one or more stimulation electrodes 220a,b, 220a',b'. In some aspects, the EEG electrodes 210 may include silver/silver chloride electrodes. In some aspects, the stimulation electrodes 220a,b, 220a',b' may include hydrogel electrodes. It may be understood that neither the EEG electrodes 210 nor the stimulation electrodes 220a,b, 220a',b' are limited to those type expressly disclosed herein. Both the EEG electrodes 210 and the stimulation electrodes 220a,b, 220a',b' may be positioned to permit contact of the respective electrode surfaces to the skin of the head. In some non-limiting examples, the headgear 100 may include multiple EEG electrodes 210. In some non-limiting examples, the headgear 100 may include one, two, three, four, or any integer number of EEG electrodes 210. Similarly, the headgear 100 may include one or more pairs of stimulation electrodes 220a,b. In some non-limiting examples, the headgear 100 may include one, two, three, four, or any integer number of pairs of stimulation electrodes 220a,b, 220a',b'.

Figure 2A:
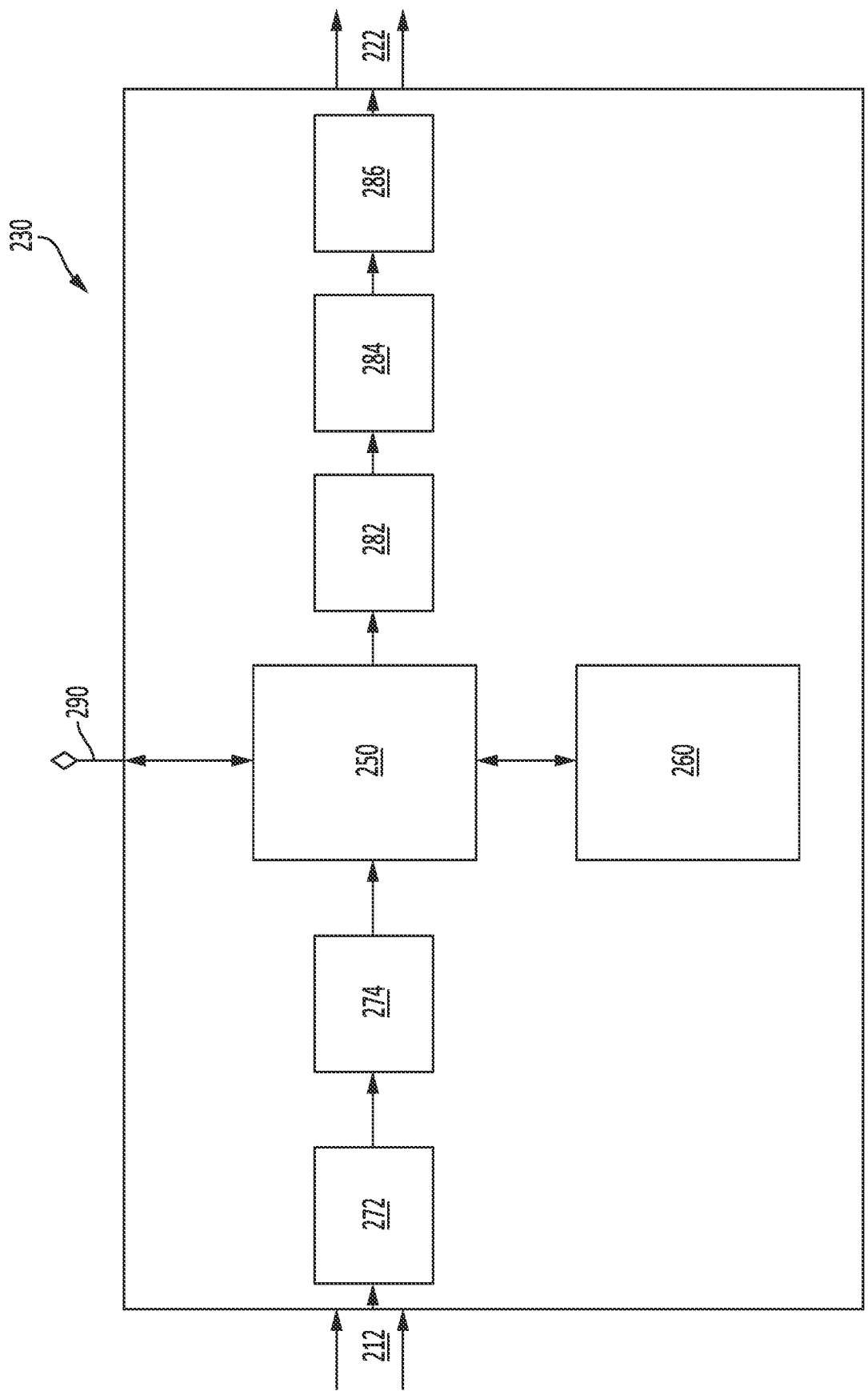
FIG. 2A depicts a detailed schematic of the control electronics illustrated in FIG. 2 according to an aspect of the present disclosure.

The headgear 100 may also include control electronics 230. The control electronics 230 are depicted schematically in greater detail in FIG. 2A. The control electronics 230 are configured to receive EEG signals 212 from the EEG electrodes 210, and to provide the transcranial stimulation current 222 to the stimulation electrodes 220a,b, 220a',b'. In some aspects, the control electronics 230 may include a processor 250 and memory component 260 configured to contain instructions that, when executed by the processor 250, cause the processor 250 to receive the EEG signals 212 from the EEG electrodes 210 and transmit transcranial stimulation current 222 to the stimulation electrodes 220a,b, 220a',b'. The control electronics 230 may also include one or more input amplifiers and/or filters 272 to obtain, amplify, and filter the EEG signals 212 received from the EEG electrodes 210. In some examples, the control electronics 230 may also include components, such as analog to digital converters 274 that may convert the amplified and filtered EEG signals to equivalent digital signals that may be received by the processor 250 and stored in the memory components 260.

The control electronics 230 may also include components including a digital to analog converter 282 to receive digital data related to a stimulation waveform from the processor 250. The digital to analog converter 282 may convert the digital stimulation signal from the processor 250 into an analogue signal that may further be amplified and filtered by an output amplifier and/or filter 284. The amplified analog stimulation signal may be sourced to a current driver 286 to provide the required analogue stimulation current 222 to the stimulation electrodes 220a,b, 220a',b'. In some aspects, the control electronics 230 may also include circuits configured to limit the output current 222 to the stimulation electrodes 220a,b, 220a',b' to a predefined value. In some aspects, the current driver 286 may include functions to limit the output current 222 to the stimulation electrodes 220a,b, 220a',b'. In one example, the output current 222 to the stimulation electrodes 220a,b, 220a',b' may be limited to about 4 mA. In another example, the output current to the stimulation electrodes may be limited to about 250 µA. Other ranges in current output values may be found between the two values. In some non-limiting examples, the output current to the stimulation electrodes 220a,b, 220a',b' may be limited to about 10 µA, about 50 µA, about 100 µA, about 150 µA, about 200 µA, about 250 µA, about 300 µA, about 350 µA, about 400 µA, about 450 µA, about 500 µA, about 550 µA, about 600 µA, about 650 µA, about 700 µA, about 750 µA, about 800 µA, about 850 µA, about 900 µA, about 950 µA, about 1 mA, about 2 mA, about 3 mA, about 4 mA, or any value or range of values therebetween.

Additionally, the control electronics 230 may include one or more antennae 290 configured to receive wireless communications from and transmit wireless communications to a mobile device. The memory component 260 may include additional instructions that, when executed by the processor 250, may cause the processor 250 to interpret the received wireless communications and execute functions according to the received communications. In one non-limiting example, the processor 250 may interpret the received wireless communications as a value or values that define a waveform of a transcranial stimulation current 222. The memory component 260 may also include instructions that, when executed by the processor 250, may cause the processor 250 to transmit wireless communications to the mobile device. The transmitted communications may include, without limitation, data regarding the state of the headgear 100, data defining one or more EEG signals 212 received from the user of the headgear 100, or other relevant data.

In some aspects, the control electronics 230 may be stored in a pouch or pocket disposed in the headband 110. The control electronics 230 may include one or more control switches to control the operation of the control electronics 230 (for example, an on/off switch). The control electronics 230 may also include one or more indicators related to the operation of the control electronics 230. For example, an optical indicator (such as indicator light 234) may indicate the power status of the control electronics 230 or the state of wireless connectivity of the control electronics 230 to a mobile communication device.

Figure 3A:
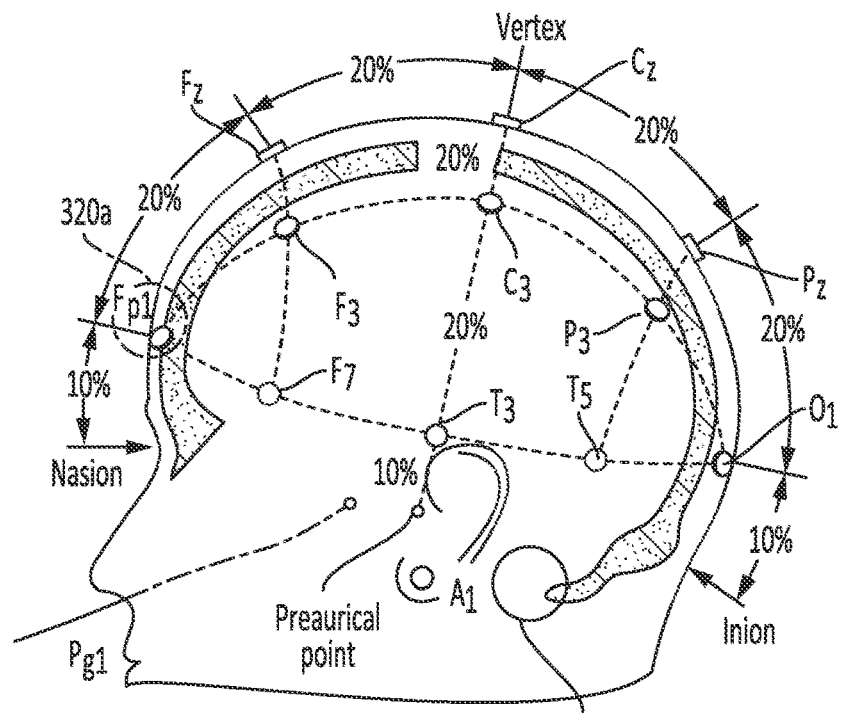
FIGS. 3A and 3B illustrate examples of positions of stimulating electrodes when the headgear is warn on the head according to an aspect of the present disclosure.
Figure 3B:
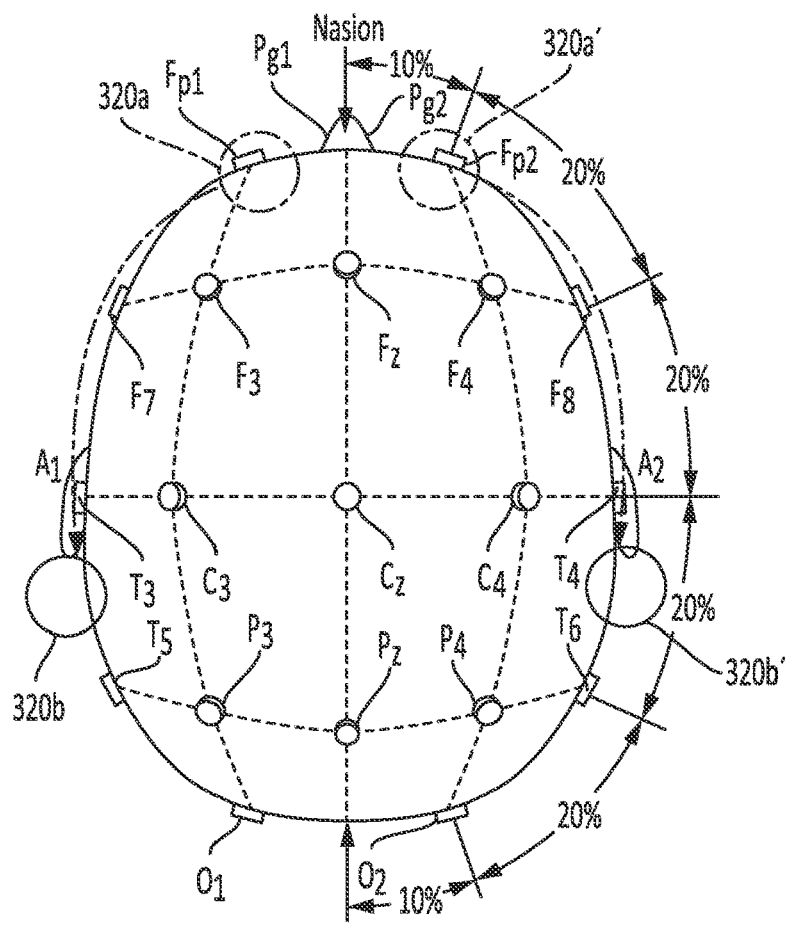

FIGS. 3A and 3B depict schematically some exemplary positions of the stimulation electrodes 220a,b, 220a',b' when positioned on a user's head. In some aspects, the stimulation electrodes 220a,b, 220a',b' may be composed of one or more pairs of electrodes. Two pairs of electrodes are depicted in FIG. 3 (320a,b and 320a',b'). Each pair of electrodes may include a front electrode (320a, 320a') and a rear electrode (320b, 320b'). In some examples, the front electrode (320a, 320a') of the electrode pair may be positioned on the forehead proximate to the frontal cortex or pre-frontal cortex. Using the internationally recognized 10-20 system of cranial electrode positioning, the front stimulation electrode(s) (320a, 320a') may be placed in the frontal polar (FP) 1 or 2 location. As illustrated in FIG. 3B, front stimulation electrode 320a may be positioned at or near (FP) 1, and front stimulation electrode 320a' may be positioned at or near (FP) 2. In an alternative example, the front stimulation electrode(s) (320a, 320a') may be place in the frontal (F) 3 or 4 position. For Example, front stimulating electrode 320a may be placed near the frontal (F) 3 position (not shown) and the front stimulating electrode 320a' may be placed near the frontal (F) 4 position (not shown). The electrode(s) placed in the F3 or F4 position may be placed proximal to the dorsal/lateral pre-frontal cortex.

The rear stimulation electrodes 320b,b' may be place on the skin overlaying the mastoid process at the A 1 or 2 location. The rear stimulation electrodes 320b,b' may be located proximal to the inferior lateral temporal cortex. It may be recognized that for each pair of stimulation electrodes 320a,b or 320a',b', the rear electrode (for example 320b) is located on the ipsilateral side of the head as the front stimulation electrode (for example 320a). The rear electrode(s) 320b,b' may be located at alternative sites at the rear of the head. However, as head hair may interfere with the ability of the rear electrodes 320b,b' to properly conduct current, the A 1 or 2 position may be preferred for most users of the headgear 100.

The one or more EEG electrodes 210 may be located at any convenient position on the user's head. As one example, and as depicted in FIG. 2, the one or more EEG electrodes 210 may be approximately co-linear with the front stimulation electrodes. Thus, the one or more EEG electrodes 210 may be located proximal to the frontal or pre-frontal lobe of the user. Again, head hair may interfere with function of the EEG electrodes 210 and may reduce the sensitivity of the EEG electrodes 210 to the EEG waveforms generated by the brain. Therefore, the one or more EEG electrodes 210 may be preferably located in the headgear 100 to make direct contact with the skin of the forehead that is proximate to the frontal or pre-frontal lobe of the user.

The headgear 100 may be incorporated into a sleep induction system. The sleep induction system may also include a mobile computing device that may include user software (such as a software application) configured to cooperate with the control electronics 230 of the headgear 100. Non-limiting examples of the mobile computing device may include a cell phone, a smart phone, a tablet computer, or similar device. The mobile computing device may communicate with the control electronics 230 over a wireless connection (such as, without limitation, Bluetooth™, Bluetooth Low Energy™, WiFi, or other wireless connection). In some aspects the mobile computing device may communicate with the control electronics 230 over a wired connection such as a serial link. It may be recognized that the mobile computing device may include a processor, a memory device, and one or more interface devices. The memory device may include instructions, as user software or application, which may be executed by the processor to effect one or more functions. The one or more interface devices may be used to receive input from a user to direct the one or more functions of the mobile device. Alternatively, the one or more interface devices may be used to provide output information to the user, for example information related to the status or function of the mobile device or of the sleep induction system. Such interface devices may include, for user input, one or more buttons, a key pad, a touch-pad, or a microphone to receive user voice commands. The user interface devices may include, for user output, one or more visual screens, light emitting sources, or audio sources.

The user software (or "app") installed on the mobile computing device may allow the user to control the operation of the control electronics 230 of the headgear 100. In one aspect, a user may use the app to initiate and stop a transcranial stimulation session. In another aspect, a user may use the app to adjust timing parameters associated with the transcranial stimulation session. In another aspect, a user may use the app to adjust a type of stimulation waveform applied to the stimulation electrodes 220a,b. In yet another aspect, a user may use the app to activate or deactivate one or more sensory stimuli that may operate concurrently with the stimulation waveform. In yet another aspect, a user may use the app to record EEG waveforms from the user while awake or asleep. In some aspects, the app resident in the mobile computing device may include a user interface which the user may use to control the functions of the app. Without limitation, the user interface may include icons which, when activated, may activate one or more functions of the app. The user interface may also include a space to receive a text instruction entered by the user (for example, through a touch screen keyboard). The user interface may also display information to the user regarding a sleep-induction protocol that the user has programmed into the mobile device. The user interface may provide any other type of useful information to the user regarding the sleep-induction system or program.

In one aspect, the sleep induction system may be used as follows. The user, while awake, may place the headgear 100 on the user's head, making required adjustments to the headband 110 to assure electrode physical contact with the appropriate portions of the head. The user may then power on the control electronics 230. The user may activate the app on the mobile device to control the transcranial stimulation current generated by the headgear 100 for a duration of a stimulation session. A stimulation session may be composed of periods of electrical stimulation separated by stimulus-free interstimulus intervals. The stimulation periods may range between about 4 seconds to about 8 seconds. Some non-limiting examples of a stimulation period may include about 4 second, about 5 second, about 6 second, about 7 second, about 8 second, or any value or range in values therebetween including endpoints. The stimulus-free interstimulus intervals may range between about 1 second to about 60 seconds. Non-limiting examples of such interstimulus time intervals may include about 1 second, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, or any value or range of values therebetween including endpoints. The stimulation session may range between about 5 minutes to about 120 minutes, in which successive stimulation periods are separated by the interstimulus intervals. Non-limiting examples of a duration of a stimulation session may include about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, or any value or range of values therebetween including endpoints.

It may be recognized that the duration of the stimulation periods, interstimulus intervals, and length of the stimulation session may be separately or jointly adjusted in order to optimize sleep induction for a particular user. In some aspects, a stimulus cycle may be composed of a single stimulation period followed by a single interstimulus interval. The stimulation session may be composed of a number of sequential stimulus cycles. Each stimulus cycle may be characterized by a stimulation duty cycle, which may be calculated as the ratio of the stimulation period to the time length of the total stimulus cycle. One may consider the exemplary values for the transcranial stimulation disclosed above in the following manner. A stimulation waveform may approximate a delta waveform, having a period between about 0.5 sec. and about 2.0 sec. A single stimulation period may have a duration ranging between about 4 sec. and about 8 sec. Thus, a single stimulation period may include about 2 delta waveforms to about 16 delta waveforms. As disclosed above, an interstimulus interval may last between about 10 seconds and about 60 seconds. By defining a stimulus cycle as being composed of one stimulation period and one interstimulus value, the stimulus cycle may range between about 14 sec and about 68 sec. In the example disclosed above, a duty cycle of such a stimulus cycle may therefore range between about 6% and about 57%. However, without being limiting, alternative duty cycles of a stimulus cycle may range between about 5% and about 95%. Non-limiting examples of a duty cycle of a stimulus cycle include about 5%, about 15%, about 25%, about 35%, about 45%, about 55%, about 65%, about 75%, about 85%, about 95%, or any value or range of values therebetween including endpoints. Thus, these parameters for a sleep-induction session—including the type of sensory stimulus, the length of the stimulation period, the length of the stimulus-free interstimulus interval, the stimulus cycle duty cycle, and length of the sleep-induction session—may all be programed in the mobile device by the user through the user interface of the app.

In some aspects, the sleep induction system may also provide additional sensory stimulus that is phase locked with the transcranial electrical stimulation. It may be understood that two signals may be considered phase-locked with respect to each other if the phase difference between the two signals does not vary (or does not vary significantly) over time. Non-limiting examples of such sensory stimuli may include visual stimuli and auditory stimuli. In some aspects, the app programmed in the mobile device may include a graphical stimulation for viewing on a visual display of the mobile device thereby providing a visual stimulus. The visual stimulus displayed on a visual display on the mobile device may include one or more visual characteristics that are modulated in concert with the transcranial electrical stimulation waveform. Non-limiting examples of such modulated visual characteristics may include display brightness, display color, a pattern that comprises the display, or any combination or combination thereof. It may be understood that modulation of the one or more visual characteristics means that the one or more visual characteristics are modulated at a frequency—or a harmonic of a frequency—of the transcranial electrical stimulation waveform. Thus, if the transcranial electrical stimulation waveform is that of a human delta-wave (having a frequency range between about 0.5 Hz and about 2 Hz), the visual characteristics may be modulated at the delta-wave frequency or any positive integer multiple (harmonic) of the delta-wave frequency.

The mobile device may also provide auditory sensory stimuli. In some examples, the auditory stimulus may be played through a speaker of the mobile device. In another example, the auditory stimulus may be provided as an output to earphones or earbuds that may be plugged into an auditory output jack of the mobile device. The auditory stimulus may include one or more auditory characteristics that are modulated in concert with the transcranial electrical stimulation waveform. Non-limiting examples of the modulating auditory characteristics may include an auditory amplitude, an auditory frequency, or a combination of the two. It may be understood that modulation of the one or more auditory characteristics means that the one or more auditory characteristics are modulated at a frequency—or a harmonic of a frequency—of the transcranial electrical stimulation waveform. Thus, if the transcranial electrical stimulation waveform is that of a human delta-wave (having a frequency range between about 0.5 Hz and about 2 Hz), the auditory characteristics may be modulated at the delta-wave frequency or any positive integer multiple (harmonic) of the delta-wave frequency.

FIG. 4 illustrates the application of the transcranial electrical stimulus along with one or more sensory stimuli for sleep induction. Depicted in FIG. 4, are a graph of electrical amplitude versus time of the transcranial electrical stimulation waveform 420, and a graph of sensory amplitude versus time of the sensory stimulation waveform 425. For example, the sensory stimulation waveform 425 may relate to an auditory stimulus. As can be seen in FIG. 4, the modulation frequency of the sensory stimulation waveform 425 has about the same frequency as the frequency of the electrical stimulation waveform 420. As also depicted in FIG. 4, the two waveforms (420 and 425) are phase-locked, as indicated by the line 427. It may be recognized that the amplitude maxima of both the transcranial electrical stimulation waveform 420 and the sensory stimulus waveform 425 are coincident. However, it may be recognized that two phase-locked signals do not need to be coincident. As disclosed above, a first signal may be phase-locked with respect to a second signal if the phase difference between the first signal and the second signal is effectively time invariant. Thus the transcranial electrical stimulation waveform 420 and the sensory stimulus waveform 425 depicted in FIG. 4 may have a phase difference of about 0, thereby being coincident. Alternatively, the transcranial electrical stimulation waveform 420 and the sensory stimulus waveform 425 may have a non-zero phase difference. As one non-limiting example, the phase difference between the transcranial electrical stimulation waveform 420 and the sensory stimulus waveform 425 may be about 180°, thereby being in an anti-phase relationship.

FIG. 5 illustrates the portions of the brain that may respond to the transcranial electrical stimulation as well as the sensory stimuli. The general geography of the human brain may include: the prefrontal cortex 510, the somatic motor association area (premotor cortex) 515, the primary motor cortex at the precentral gyrus 520, the primary sensory cortex at the postcentral gyrus 525, the somatic sensory association area 530, the visual association area 535, the visual cortex 540, the speech cortex (Wernicke's area) 545, the auditory cortex 550, the auditory association area 555, and Broca's area (speech production) 560. In reference to FIGS. 3A, B, the front transcranial electrical stimulation electrodes 320a,a', may be located adjacent to the prefrontal cortex 510, for example at 580. It may be recognized that the pairing of a visual stimulus with the transcranial electrical stimulus may result in coordinated stimulation of regions 582 close to or including the visual association area 535 and the visual cortex 540. Similarly, it may be recognized that the pairing of an auditory stimulus with the transcranial electrical stimulus may result in coordinated stimulation of regions 584 close to or including the speech cortex (Wernicke's area) 545, the auditory cortex 550, and the auditory association area 555.

The transcranial electrical stimulation may have a waveform similar to that generated by a user's brain during sleep, for example during non-REM stage 3 sleep. FIG. 6 depicts an example of such an EEG waveform 600 having amplitudes measured in µV and time in seconds. The waveform may have a relatively large amplitude (peak to trough) and may be characterized by a period corresponding to a frequency in the range of about 0.5 Hz to about 2 Hz. Non-limiting examples of the frequency of the waveform may include about 0.5 Hz, about 0.55 Hz, about 0.6 Hz, about 0.65 Hz, about 0.7 Hz, about 0.75 Hz, about 0.8 Hz, about 0.85 Hz, about 0.9 Hz, about 0.95 Hz, about 1.0 Hz, about 1.5 Hz, about 2.0 Hz, or any value or range of values therebetween including endpoints. This frequency may correspond to the frequency of low delta waves 610 of a sleeping user.

In one example, a transcranial electrical stimulation waveform may be characterized by a frequency of about 0.75 Hz. In some examples, as depicted in FIG. 7, the transcranial electrical stimulation waveform 710 may be one recorded from a sleeping patient (see segment 610 from the recorded EEG signal 600 of FIG. 6). This recorded low delta waveform may have a bi-polar voltage range in amplitude values (both positive and negative). In some alternative examples, as depicted in FIG. 8A, the transcranial electrical stimulation waveform 810 may be a recorded low delta waveform that is amplitude shifted to mono-polar (only positive values) range. In yet another example, as depicted in FIG. 8B, the transcranial electrical stimulation waveform 815 may be a mono-polar envelope of an amplitude shifted recorded low delta waveform.

In some aspects, the transcranial electrical stimulation waveform may have been previously recorded from the user. In this aspect, the user may wear the headgear 100 during sleep and the EEG electrodes 210 may record the EEG activity 600 of the user during sleep. The app on the mobile device may have a function that permits it to receive, analyze, and record the EEG activity 600 of the user during sleep. The app may include algorithms that specifically detect non-REM stage sleep activity and record the appropriate low delta phase EEG signal (for example 610). The app may then use this waveform (for example as 710) as the transcranial electrical stimulation waveform during sleep induction. In one aspect, the low delta waveform may be constructed from an ensemble average of low delta waveforms from multiple recordings of the user during sleep. In another aspect, the low delta waveform may be constructed from an ensemble average of low delta waveforms recorded from a plurality of sleepers. In this instance, the specific user may not be required to wear the headgear during sleep in order to record a user-specific waveform. According to one aspect, the mobile device app may be configured to transmit information that characterizes the transcranial stimulation waveform to the control electronics 230 of the headgear 100. In some aspects, the user may determine which type of waveform—user specific, amplitude shifted, waveform envelope, or ensemble waveform—to use during sleep induction. The user may configure the mobile device app to transmit the required waveform to the headgear.

FIG. 9 summarizes one aspect of a method of use of the system for inducing sleep. In one example, the user may employ the app on the mobile device to select a type of transcranial stimulatory waveform and a type of sensory stimulatory waveform 910. As disclosed above, the user may select parameters to control both waveforms (such as a stimulation period and a length of inter-stimulus interval). The user may also select a length of time for a stimulation session (defined by a number of stimulation periods separated by inter-stimulus intervals). In some cases, the user may also be able to control the amplitudes of the transcranial stimulatory waveform and the sensory stimulatory waveform. In some cases, a health-care professional may determine the characteristics of the waveforms. The system, based on the control software in the app, may then apply both the transcranial stimulatory waveform 915 and the sensory stimulatory waveform 920, coordinating their respective modulations. These stimulations may then be applied to the user before the user goes to bed.

Having shown and described various aspects of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, the examples, aspects, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

While various details have been set forth in the foregoing description, it will be appreciated that the various aspects of the system and method for using sleep enhancement during sleep may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various embodiments are described in the following numbered examples:

Example 1. A device for inducing sleep in a waking user, the device comprising:
  a headgear comprising:
    a headband;
    a plurality of transcranial stimulation electrodes disposed within the headband; and
    a control system disposed within the headband and in electrical communication with the plurality of transcranial stimulation electrodes, wherein the control system comprises:
      a processor; and
      a memory device configured to store instructions that, when executed by the processor, cause the processor to, alternately:
        transmit a transcranial stimulation current to the plurality of transcranial stimulation electrodes for a first period of time; and
        cease transmission of the transcranial stimulation current for a second period of time,
        wherein the transcranial stimulation current is characterized by a transcranial stimulation waveform, and
        wherein the transcranial stimulation waveform has an amplitude characteristic and a frequency characteristic of a low-delta waveform.

Example 2. The device of Example 1, wherein the transcranial stimulation waveform has a frequency between about 0.5 Hz and about 4 Hz.

Example 3. The device of any one or more of Example 1 through Example 2, wherein the transcranial stimulation waveform has a frequency of about 0.75 Hz.

Example 4. The device of any one or more of Example 1 through Example 3, wherein the first period of time is about 4 sec to about 8 sec.

Example 5. The device of any one or more of Example 1 through Example 4, wherein the second period of time is about 10 sec to about 30 sec.

Example 6. The device of any one or more of Example 1 through Example 5, wherein the plurality of transcranial stimulation electrodes comprises a plurality of pairs of transcranial stimulation electrodes.

Example 7. The device of Example 6, wherein each of the plurality of pairs of transcranial stimulation electrodes comprises a front stimulation electrode and a rear stimulation electrode.

Example 8. The device of any one or more of Example 1 through Example 7, wherein in the control system further comprises one or more antennas configured to transmit and receive a wireless communication signal.

Example 9. The device of any one or more of Example 1 through Example 8, further comprise one or more EEG electrodes, and the a memory device further stores instructions that, when executed by the processor, cause the processor to receive and store one or more EEG waveforms received from the one or more EEG electrodes.

Example 10. A system for inducing sleep in a waking user, the system comprising:
  a mobile communication device; and
  a headgear comprising:
    a headband;
    a plurality of transcranial stimulation electrodes; and
    a control system disposed within the headband and in electrical communication with the plurality of transcranial stimulation electrodes, wherein the control system comprises:
      an antenna configured to receive wireless communications signals from the mobile communication device;
      a processor in data communication with the antenna; and
      a memory device configured to store instructions that, when executed by the processor, cause the processor to:
        receive, via the antenna, one or more signals transmitted by the mobile communication device;
        transmit a transcranial stimulation current to the plurality of transcranial stimulation electrodes for a first period of time based on the one or more signals received from the mobile communication device; and
        cease transmission of the transcranial stimulation current for a second period of time based on the one or more signals received from the mobile communication device,
        wherein the transcranial stimulation current is characterized by a transcranial stimulation waveform, and
        wherein the transcranial stimulation waveform has an amplitude characteristic and a frequency characteristic of a low-delta waveform.

Example 11. The system for inducing sleep in a waking user of Example 10, wherein the one or more signals transmitted by the mobile communication device to the antenna comprise data to characterize the transcranial stimulation current.

Example 12. The system for inducing sleep in a waking user of Example 11, wherein the mobile communication device is configured to emit a sensory stimulation signal that is delivered with a consistent delay with respect to the waveform of the transcranial stimulation current.

Example 13. The system for inducing sleep in a waking user of Example 12, wherein the sensory stimulation signal comprises an audible signal or a visible signal.

Example 14. The system for inducing sleep in a waking user of Example 13, wherein an amplitude of the audible signal or an amplitude of the visible signal is modulated at a positive integer multiple of the frequency characteristic of the transcranial stimulation waveform.

Example 15. The system for inducing sleep in a waking user of any one or more of Example 11 through Example 14, wherein the mobile communication device comprises a second processor and a second memory device, and one or more user interfaces, wherein the second memory device is configured to store instructions that, when executed by the second processor, causes the second processor to receive, via the one or more user interfaces, data input from a user.

Example 16. The system for inducing sleep in a waking user of Example 15, wherein the data input from the user comprise the data to characterize the transcranial stimulation current.

Example 17. The system for inducing sleep in a waking user of any one or more of Example 15 through Example 16, wherein the data input from the user comprise data to characterize a sensory stimulation signal emitted by the mobile communication device.

Example 18. The system for inducing sleep in a waking user of any one or more of Example 10 through Example 17, wherein the transcranial stimulation waveform has an amplitude characteristic and a frequency characteristic of an EEG waveform recorded from the waking user when the waking user is sleeping.

What is claimed is:

1. A system for inducing sleep in a waking user, the system comprising:
    a mobile communication device; and
    a headgear comprising:
        a headband;
        a plurality of transcranial stimulation electrodes; and
        a control system disposed within the headband and in electrical communication with the plurality of transcranial stimulation electrodes, wherein the control system comprises:
            an antenna configured to receive wireless communications signals from the mobile communication device;
            a processor in data communication with the antenna; and
            a memory device comprising instructions that, when executed by the processor, cause the processor to:
                receive, via the antenna, one or more signals transmitted by the mobile communication device;
                transmit a transcranial stimulation current to the plurality of transcranial stimulation electrodes for a first period of time based on the one or more signals received from the mobile communication device; and
                cease transmission of the transcranial stimulation current for a second period of time based on the one or more signals received from the mobile communication device,
            wherein the transcranial stimulation current is characterized by a transcranial stimulation waveform,
            wherein the transcranial stimulation waveform has an amplitude characteristic and a frequency characteristic of a low-delta waveform, and
            wherein the mobile communication device is to emit a sensory stimulation signal that is phase-locked with respect to the waveform of the transcranial stimulation current.

2. The system of claim 1, wherein the transcranial stimulation waveform has a frequency between 0.5 Hz and 4 Hz.

3. The system of claim 1, wherein the transcranial stimulation waveform has a frequency of 0.75 Hz.

4. The system of claim 1, wherein the first period of time is 4 sec to 8 sec.

5. The system of claim 1, wherein the second period of time is 10 sec to 30 sec.

6. The system of claim 1, wherein the plurality of transcranial stimulation electrodes comprises a plurality of pairs of transcranial stimulation electrodes.

7. The system of claim 6, wherein each of the plurality of pairs of transcranial stimulation electrodes comprises a front stimulation electrode and a rear stimulation electrode.

8. The system of claim 1, further comprise one or more EEG electrodes, and the memory device further stores instructions that, when executed by the processor, cause the processor to receive and store one or more EEG waveforms received from the one or more EEG electrodes.

9. The system for inducing sleep in a waking user of claim 1, wherein the one or more signals transmitted by the mobile communication device to the antenna comprise data to characterize the transcranial stimulation current.

10. The system for inducing sleep in a waking user of claim 9, wherein the mobile communication device comprises a second processor and a second memory device, and one or more user interfaces, wherein the second memory device is configured to store instructions that, when executed by the second processor, causes the second processor to receive, via the one or more user interfaces, data input from the waking user.

11. The system for inducing sleep in a waking user of claim 10, wherein the data input from the user comprises the data to characterize the transcranial stimulation current.

12. The system for inducing sleep in a waking user of claim 10, wherein the data input from the user comprises data to characterize a sensory stimulation signal emitted by the mobile communication device.

13. The system for inducing sleep in a waking user of claim 1, wherein the sensory stimulation signal comprises an audible signal or a visible signal.

14. The system for inducing sleep in a waking user of claim 13, wherein an amplitude of the audible signal or an amplitude of the visible signal is modulated at a positive integer multiple of the frequency characteristic of the transcranial stimulation waveform.

15. The system for inducing sleep in a waking user of claim 1, wherein the transcranial stimulation waveform has an amplitude characteristic and a frequency characteristic of an EEG waveform recorded from the waking user when the waking user is sleeping.

* * * * *